United States Patent
Karami et al.

(10) Patent No.: US 9,447,014 B2
(45) Date of Patent: Sep. 20, 2016

(54) TROMETHAMINE SALT OF BIMATOPROST ACID IN CRYSTALLINE FORM, METHODS FOR PREPARATION, AND METHODS FOR USE THEREOF

(71) Applicant: ALLERGAN, INC., Irvine, CA (US)

(72) Inventors: Thomas K. Karami, Aliso Viejo, CA (US); Scott W. Smith, Mission Viejo, CA (US); Fiona Dubas-Fisher, Ely (GB); Adrian St. Clair Brown, Ely (GB)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/137,447

(22) Filed: Dec. 20, 2013

(65) Prior Publication Data

US 2014/0187637 A1     Jul. 3, 2014

Related U.S. Application Data (60) Provisional application No. 61/746,726, filed on Dec. 28, 2012.

(51) Int. Cl.
  *C07C 59/54*   (2006.01)
  *C07C 215/10*  (2006.01)
  *C07C 405/00*  (2006.01)

(52) U.S. Cl.
  CPC ............ *C07C 59/54* (2013.01); *C07C 215/10* (2013.01); *C07C 405/00* (2013.01); *C07B 2200/13* (2013.01); *C07C 2101/08* (2013.01)

(58) Field of Classification Search
  CPC .................................................. C07C 59/54
  See application file for complete search history.

(56) References Cited

U.S. PATENT DOCUMENTS

| 4,556,413 A | 12/1985 | Hoffmann |
| 8,629,185 B2 | 1/2014 | Ambrus et al. |
| 2009/0163596 A1 | 6/2009 | Gutman et al. |
| 2010/0105775 A1 | 4/2010 | Delong |
| 2014/0187636 A1 | 7/2014 | Wu et al. |

FOREIGN PATENT DOCUMENTS

| EP | 0109575 A2 | 5/1984 |
| WO | 9800100 | 1/1998 |
| WO | 2011063276 | 5/2011 |
| WO | 2012164324 A1 | 12/2012 |

(Continued)

OTHER PUBLICATIONS

International Searching Authority, Notification of Transmittal of International Search Report and the Written Opinion of the International Searching Authority, or the Declaration, Date of Mailing Apr. 8, 2014, International Application No. PCT/US2013/078356.

(Continued)

*Primary Examiner* — Zohreh Fay
(74) *Attorney, Agent, or Firm* — Jonathan Bass (57) ABSTRACT

The present invention provides tromethamine salt of 7-[3, 5-Dihydroxy-2-(3-hydroxy-5-phenyl-pent-1-enyl)-cyclopentyl]-hept-5-enoic acid in crystalline and amorphous form. This compound is may also be referred to as "tromethamine salt of bimatoprost acid." The invention crystalline form is useful for solid ocular implant or topical formulations, utilized in the treatment of various ocular conditions, such as, for example, ocular hypertension.

20 Claims, 7 Drawing Sheets

DSC data for Bimatoprost Acid (crystalline anhydrous) compared to the Tromethamine Salt of Bimatoprost Acid (crystalline Form 1) that is indicating a melting temperature for the salt at about ~40°C higher than melting temperature of the free acid.

(56) References Cited

FOREIGN PATENT DOCUMENTS

| WO | 2014006204 | 7/2014 |
|----|------------|--------|
| WO | 2014106194 | 7/2014 |

OTHER PUBLICATIONS

Bito, LZ, Biological Protection with Prostanoids, CRC Press, Inc., 1985, 231-252, 1, Cohen, M. M., ed., Boca Raton, Fla.

L.Z. Bito, Glaucoma: Applied Pharmacology in Medical Treatment, Prostaglandins, Other Eicosanoids, and Their Derivatives as Potential Antiglaucoma Agents, 1984, 477-505, Chapter 20.

Starr, Michael, Further Studies on the Effects of Prostagladin on Intraocular Pressure in the Rabbit, Exp. Eye Res., 1971, 170-177, 11.

International Search Report & Written Opinion mailed on Feb. 25, 2015 for PCT/US2014/044658 filed on Jun. 27, 2014 in the name of Allergan, Inc.

Final Office Action mailed on Jan. 25, 2016 for U.S. Appl. No. 14/318,402, filed Jun. 27, 2014 in the name of Thomas K. Karami et al.

Non-Final Office Action mailed on Aug. 6, 2015 for U.S. Appl. No. 14/318,402, filed Jun. 27, 2014 in the name of Thomas K. Karami et al.

Figure 1: DSC data for Bimatoprost Acid (crystalline anhydrous) compared to the Tromethamine Salt of Bimatoprost Acid (crystalline Form 1) that is indicating a melting temperature for the salt at about ~40°C higher than melting temperature of the free acid.

Figure 2: DSC/TGA analyses of Tromethamine Salt of Bimatoprost Acid (Form 1)

Figure 3: XRPD patterns of Tromethamine Salt of Bimatoprost Acid (Form 1) before and after drying process.

Figure 4: $^1$H-NMR of Tromethamine Salt of Bimatoprost Acid (Form 1 dissolved in DMSO). The absence of $^1$H-NMR peak for the -COOH proton at about 12 ppm indicates formation of the salt.

Figure 5: pH-Solubility of Tromethamine Salt of Bimatoprost Acid: the intrinsic solubility is 1.385 mg/mL at pH 2 (solubility of the free acid). Solubility of the salt at pH above 6.5 is measured as higher than 250 mg/mL (≥ 25 w/v%).

Figure 6: XRPD pattern of Tromethamine Salt of Bimatoprost Acid (Form 1) include peak positions (2-theta) for the Characteristic peaks.

Figure 7: XRPD pattern and microscopy of amorphous Tromethamine Salt of Bimatoprost Acid with its characteristic halo.

Figure 8: The glass transition (Tg) of amorphous Tromethamine Salt of Bimatoprost Acid obtained at ca. 29 °C by Modulated Differential Scanning Calorimetry (MDSC).

TROMETHAMINE SALT OF BIMATOPROST ACID IN CRYSTALLINE FORM, METHODS FOR PREPARATION, AND METHODS FOR USE THEREOF

CROSS REFERENCE TO RELATED APPLICATION

This application claims the benefit of U.S. Provisional Application Ser. No. 61/746,726, filed Dec. 28, 2012, the disclosure of which is hereby incorporated in its entirety herein by reference.

FIELD OF THE INVENTION

The present invention relates generally to tromethamine salt of bimatoprost acid and its crystalline form (Form 1) and its amorphous form. The present invention further relates to methods for its preparation and to methods for treating disorders associated with ocular hypertension and other therapeutic conditions.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. Exp. Eye Res. 1971, 11, pp. 170-177; Bito, L. Z. Biological Protection with Prostaglandins Cohen, M. M., ed., Boca Raton, Fla. CRC Press Inc., 1985, pp. 231-252; and Bito, L. Z., Applied Pharmacology in the Medical Treatment of Glaucomas Drance, S. M. and Neufeld, A. H. eds., New York, Grune & Stratton, 1984, pp. 477-505). Such prostaglandins include $PGF_{2\alpha}$, $PGF_{1\alpha}$ $PGE_2$, and certain lipid-soluble esters, such as $C_1$ to $C_5$ alkyl esters, e.g. 1-isopropyl ester, of such compounds.

It is known however that many drug compounds exist in two or more crystalline forms, referred to as polymorphs. These polymorphs of the same molecule have identical chemical properties but may exhibit different physical properties, such as melting point, solubility, hardness, etc. In such cases, the danger exists of less soluble polymorphic forms precipitating from a solution made from another more soluble but less stable form. The formation of crystals in an ophthalmic solution can cause serious injury to the eye. In addition, precipitation of the drug substance may cause an apparent reduction in potency and bioavailability of the product.

SUMMARY OF THE INVENTION

The present invention provides tromethamine salt of bimatoprost acid (7-[3,5-Dihydroxy-2-(3-hydroxy-5-phenyl-pent-1-enyl)-cyclopentyl]-hept-5-enoic acid) in its crystalline form (Form 1) and amorphous form. This compound may also be referred to as "tromethamine salt of bimatoprost acid." The invention crystalline form is useful for solid ocular implant formulations and topical ophthalmic compositions, which can be utilized in the treatment of various ocular conditions, such as, for example, ocular hypertension. In addition, the invention crystalline form is useful for solid or semisolid dosage formulations used to treat ocular hypertension. The crystalline form of tromethamine salt of bimatoprost acid may also be used in suspension, microsuspension or nanosuspension formulations for treatment of hair growth (eyelash, eyebrow, scalp) and in localized fat reduction.

In another embodiment of the invention, there is provided pharmaceutical compositions including a therapeutically effective amount of tromethamine salt of bimatoprost acid in crystalline form in an ophthalmically acceptable carrier therefore.

In another embodiment, there provided methods for treating ocular hypertension. Such methods can be performed, for example, by administering to a subject in need thereof a therapeutically effective amount of tromethamine salt of bimatoprost acid in crystalline form in an ophthalmically acceptable carrier wherein the carrier may be a solution, emulsion or suspension.

In another embodiment, there provided methods for treating glaucoma. Such methods can be performed, for example, by administering to a subject in need thereof a therapeutically effective amount of tromethamine salt of bimatoprost acid in crystalline form in an ophthalmically acceptable carrier such as a topical ophthalmic solutions administered as eye drops.

Figure 3:
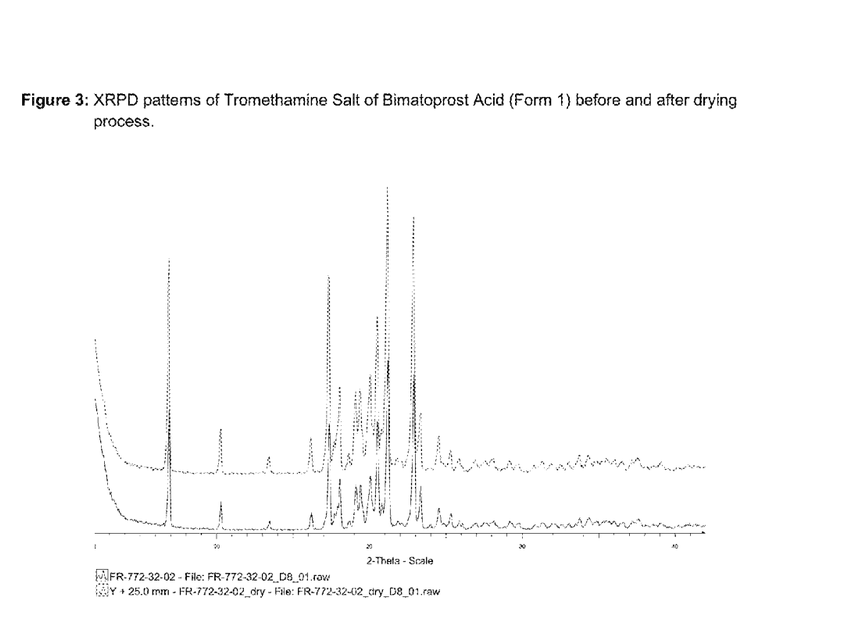
FIG. 3 shows XRPD patterns of Tromethamine Salt of Bimatoprost Acid (Form 1)
Figure 4:
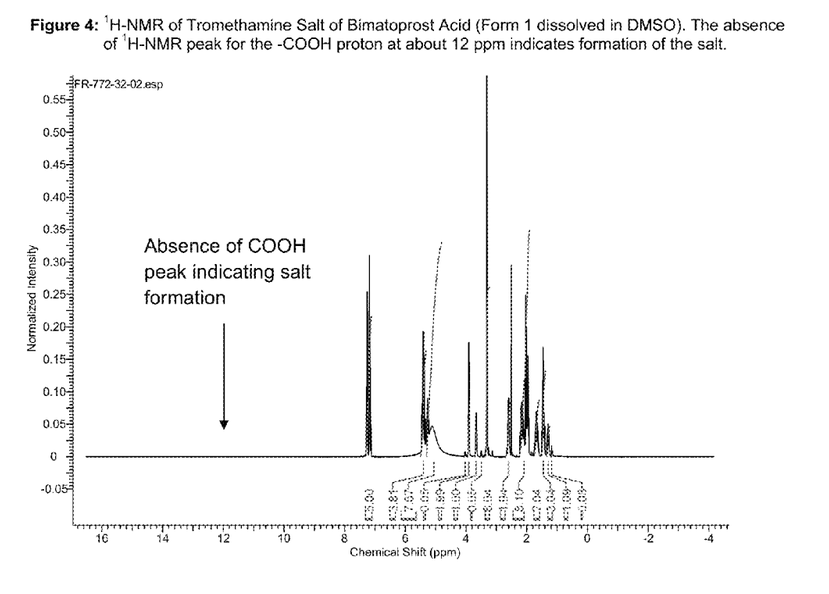
FIG. 4 shows the $^1$H-NMR of Tromethamine Salt of Bimatoprost Acid (Form 1)
Figure 5:
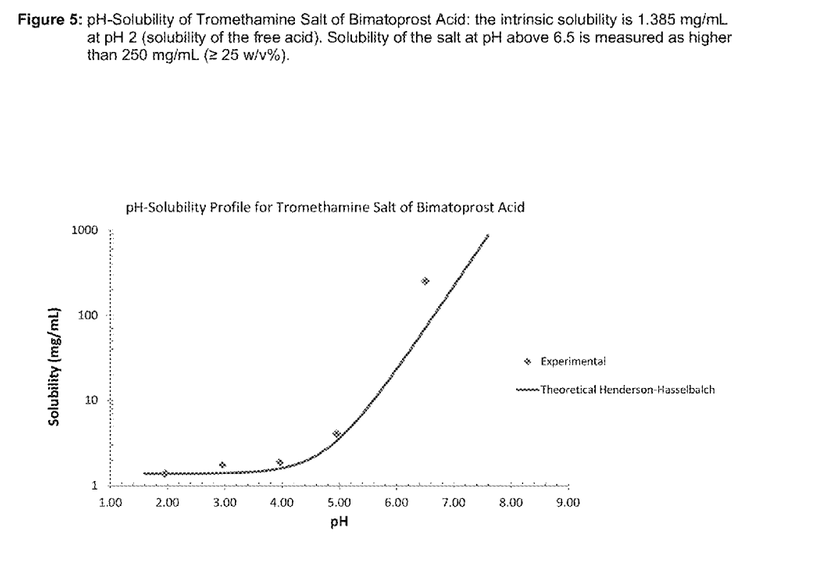
FIG. 5 shows the pH-Solubility of Tromethamine Salt of Bimatoprost Acid (Form 1)

Some embodiments of the present invention are in the following paragraphs:

1. Tromethamine salt of bimatoprost acid in crystalline form.
2. The crystalline form of paragraph 1 having the XRPD pattern substantially as shown in FIG. 3.

Figure 6:
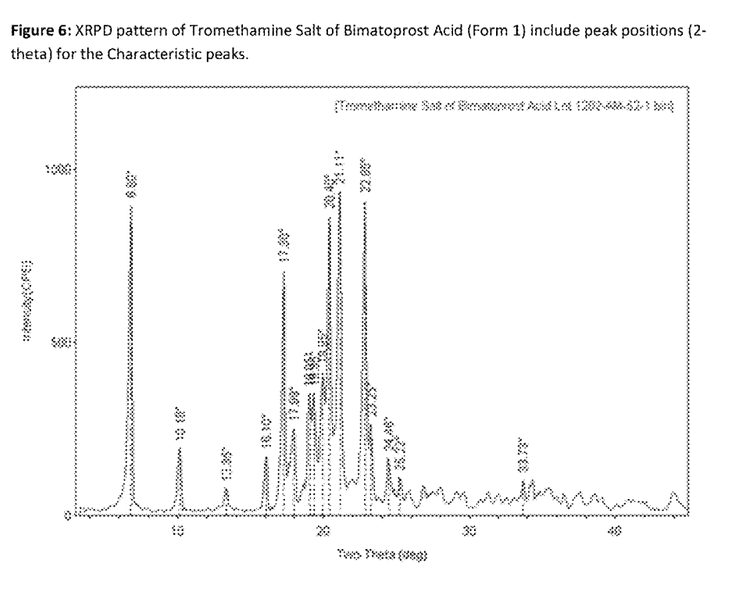
FIG. 6 shows the XRPD pattern of Tromethamine Salt of Bimatoprost Acid (Form 1) include peak positions (2-theta) for the Characteristic peaks.

3. The crystalline form of tromethamine salt of bimatoprost acid of paragraphs 1 and 2 having XRPD peaks at the diffraction angles of about: 6.8°, 10.2°, 13.4°, 16.1°, 17.3°, 18.0°, 19.1°, 19.4°, 20.0°, 20.4°, 21.1°, 22.9°, 23.3°, 24.5°, 25.2° and 33.7° of 2-theta (Cu, K-alpha radiation).
4. The crystalline form of tromethamine salt of bimatoprost acid of paragraphs 1 and 2 having XRPD peaks at the diffraction angles of about: 6.80°, 10.18°, 13.35°, 16.10°, 17.30°, 17.99°, 19.05°, 19.35°, 19.95°, 20.40°, 21.11°, 22.85°, 23.25°, 24.46°, 25.22° and 33.73° of 2-theta (Cu, K-alpha radiation) and as shown in FIG. 6.
5. The crystalline form of paragraphs 1 and 2 having a melting enthalpy from about 103.6 J/g to about 119.9 J/g.
6. The crystalline form of paragraphs 1 and 2 having a melting temperature within the range of about 104-110° C.
7. The crystalline form of paragraphs 1, 2 and 4 having a melting temperature of about 105° C.
8. The crystalline form of paragraphs 1, 2, 5 and 6 having a melting temperature of about 105.6° C.
9. A pharmaceutical composition comprising a therapeutically effective amount of tromethamine salt of bimatoprost acid in crystalline form or amorphous form.
10. The pharmaceutical composition of paragraph 9 wherein the tromethamine salt of bimatoprost acid in crystalline form is in a pharmaceutically acceptable carrier.
11. The pharmaceutical composition of paragraphs 9 and 10 wherein the pharmaceutically acceptable carrier is an aqueous solution.
12. The pharmaceutical composition of paragraph 11 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizes and combinations thereof.
13. The pharmaceutical composition of paragraph 10 wherein the pharmaceutically acceptable carrier is a solid dosage form.
14. The pharmaceutical composition of paragraphs 10 and 13 wherein the solid dosage form is an ocular implant.
15. The pharmaceutical composition of paragraph 9 wherein the pharmaceutical composition may be used to treat one selected from the group consisting of elevated intraocular pressure, glaucoma, localized fat reduction or promotion of hair growth.
16. The pharmaceutical composition of paragraph 14 wherein the ocular implant is used to treat elevated intraocular pressure or glaucoma.
17. The pharmaceutical composition of paragraph 11 wherein the bimatoprost acid in crystalline form is present in a concentration of 0.01% w/v to 0.1% w/v.
18. The pharmaceutical composition of paragraphs 11 and 17 wherein the bimatoprost acid in crystalline form is present in a concentration of 0.03% w/v.
19. A method for treating ocular hypertension comprising administering to a subject in need thereof a therapeutically effective amount of tromethamine salt of bimatoprost acid in crystalline form in an ophthalmically acceptable carrier.
20. The method of paragraph 19 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.
21. The method of paragraphs 19 and 20 wherein the tromethamine salt of bimatoprost acid in crystalline or amorphous form is dosed at least once a day.
22. The method paragraph 21 wherein the tromethamine salt of bimatoprost acid in crystalline or amorphous form is dosed once a day.
23. A method of treating ocular hypertension comprising administering to a subject in need thereof a therapeutically effective amount of amorphous tromethamine salt of bimatoprost acid in an ophthalmically acceptable carrier.
24. The composition or method of paragraphs 1, 12, 13, 14, 15, 19, 20, 21, 22 and 23 wherein the concentration of the active is selected from 0.01, 0.02, 0.03, 0.04. 0.05, 0.06, 0.07, 0.08, 0.09, 0.1, 0.2, 0.3, 0.4. 0.5, 0.6, 0.7, 0.8, 0.9 to 1.0% w/v.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

It is to be understood that "7-[3,5-Dihydroxy-2-(3-hydroxy-5-phenyl-pent-1-enyl)-cyclopentyl]-hept-5-enoic acid" and "bimatoprost acid" refer to the same compound and may be used interchangeably throughout. In addition "tromethamine salt of 7-[3,5-Dihydroxy-2-(3-hydroxy-5-phenyl-pent-1-enyl)-cyclopentyl]-hept-5-enoic acid" and "tromethamine salt of bimatoprost acid" and "Bimatoprost Tromethamine Salt" refer to the same compound and may be used interchangeably throughout.

'Crystalline form' and "polymorphic form" and ("Form 1") may be used interchangeably throughout the specification.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

Figure 1:
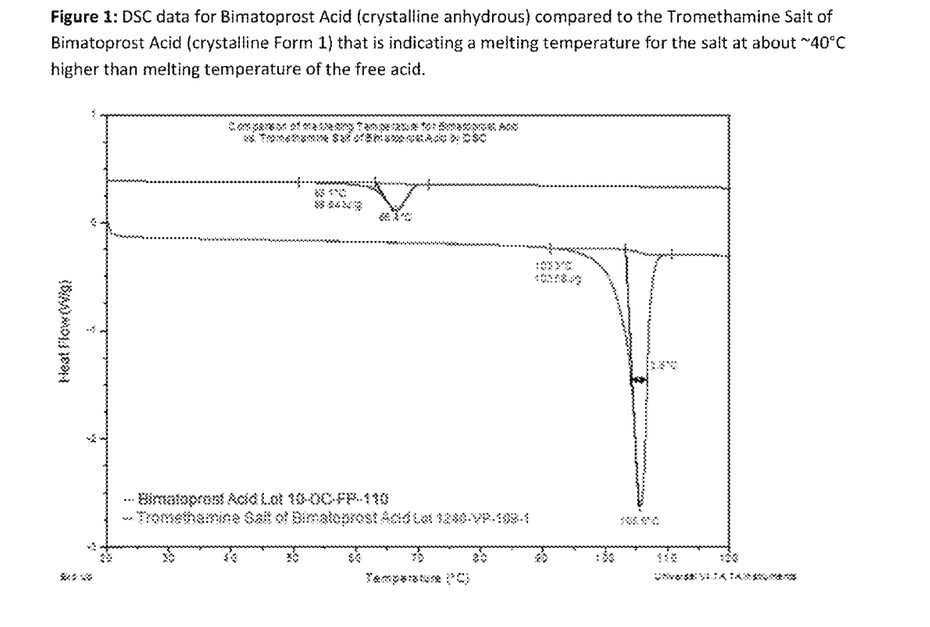
FIG. 1 shows DSC data for Bimatoprost Acid as compared to the Tromethamine Salt of Bimatoprost Acid (Form 1)

The present invention provides tromethamine salt of bimatoprost acid in crystalline and amorphous forms. Tromethamine salt of bimatoprost acid has the structure:

The crystalline form of the tromethamine salt of bimatoprost acid has advantages over the crystalline free acid, such as a significantly higher melting temperature (~40° C.) (see FIG. 1). This makes the crystalline form desirable (because the form does not change) for hot melt extrusion and process manufacturing of solid dosage forms such as implants and tablets. The salt has shown feasibility for extrusion and is physical stability for >3 months at 25° C./60% RH in open container closure and >3 months at 40° C./75% RH in closed container closure. Further, the tromethamine salt has a high solubility (>250 mg/mL at pH 6.5) and a faster dissolution rate than the free acid.

Pharmaceutical compositions may be prepared by combining a therapeutically effective amount of tromethamine salt of bimatoprost acid in crystalline form according to the invention, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations, or preferably about 0.01- to about 0.1% w/v and 0.01% w/v to about 0.03% w/v. An "effective amount" is an amount sufficient to accomplish a stated purpose (e.g., achieve the effect for which it is administered, treat a disease, reduce one or more symptoms of a disease or condition). An example of an "effective amount" is an amount sufficient to contribute to the treatment, prevention, or reduction of a symptom or symptoms of a disease, which can be referred to as a "therapeutically effective amount." A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated.

Method of making Amorphous Form of Bimatoprost Tromethamine Salt:

Attempts were made to prepare amorphous tromethamine salt of bimatoprost acid by freeze drying (using a mixture of tert-butanol/water (50/50 v/v) as solvent), rotary evaporation and quenching the melt. The most suitable method, quenching the melt, was selected for the preparation of the amorphous material, followed by characterization before using this material as input material for the polymorphism study. In an attempt, Tromethamine Salt of Bimatoprost acid was heated in a vacuum oven at 120° C., the temperature was maintained for 10 minutes to melt the product. The samples were quenched in air and then cooled to −20° C. (freezer) to obtain an amorphous glass. The glass transition (Tg) was determined at ca. 29° C. by modulated differential scanning calorimetry (MDSC).

Characterization of Crystalline Form 1 is summarized in Table 1:

TABLE 1

Characterization of the Supplied Batch of Tromethamine Salt of Bimatoprost Acid (Form 1)

| Technique | Results |
|---|---|
| XRPD | Crystalline-Form 1 |
| 1H NMR | Consistent with structure. |
| | 1.0 eq. of tromethamine. |
| | Do we need to include this information. |
| Thermal Data | TGA: Loss of 1.0% w/w from 40° C. to 150° C. (Process solvent). |
| | Loss of 25.4% w/w from 150° C. to 350° C. (possible salt dissociation, theoretical value for the loss of tromethamine: 23.7% w/w). |
| | DSC: melting onset at 107.2° C. (ΔHf = −107.87 J/g). |
| GVS analysis | 90% RH, no deliquescence, no hydrate formed. |

The supplied batch is consistent with the reference material previously prepared for this compound (Form 1). $^1$H-NMR analysis of the supplied material was consistent with the structure of the salt, 1.0 equivalent (eq.) of the counter ion (tromethamine),and 1.0 eq. of the free acid (Bimatoprost Acid).

Figure 2:
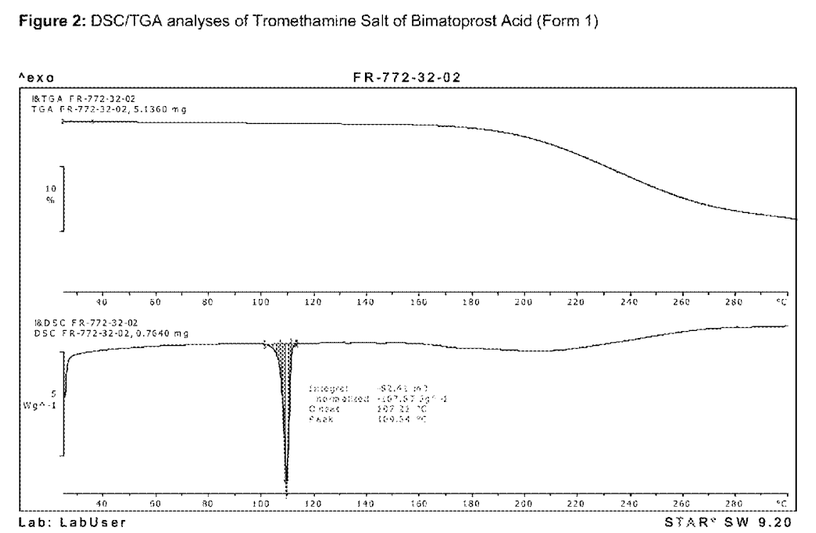
FIG. 2 shows the DSC/TGA analyses of Tromethamine Salt of Bimatoprost Acid (Form 1)

At relative humidity above 80% RH, tromethamine salt of bimatoprost acid behaves hygroscopic with a a significant moisture uptake observed. The significant uptake of moisture may be a result of the large specific surface area of the material. On desorption, the adsorbed water was rapidly lost with no equilibrium established. At the end of the gravimetric vapor sorption (GVS) cycle, at 40% RH, the overall sample mass increased by 5 wt %. XRPD re-analysis of the sample post GVS analysis showed no change in the crystalline Form 1. Thermal analyses by TGA and DSC showed that the tromethamine salt of bimatoprost acid melts at about 107.2° C. followed by a weight loss consistent with the dissociation of the salt (FIG. 2).

Figure 7:
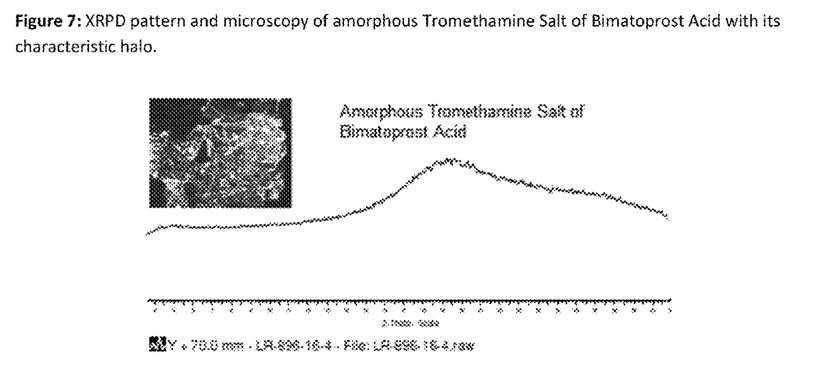
FIG. 7 shows the XRPD pattern and microscopy of Tromethamine Salt of Bimatoprost Acid; and,
FIG. 8 shows the glass transition temperature of amorphous Tromethamine Salt of Bimatoprost Acid by MDSC.
Figure 8:
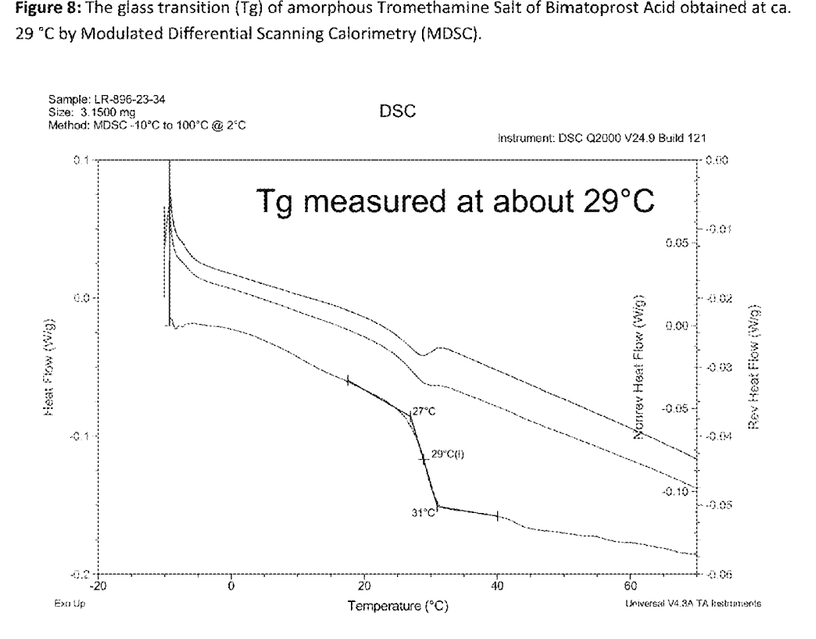

Characterization of Amorphous Tromethamine Salt of Bimatoprost Acid:

The most suitable method for the generation of amorphous material was quenching the melt. The characterization of the prepared amorphous material is summarized in Table 2. The broad X-ray powder diffraction pattern obtained from the amorphous material showed a continuous intensity distribution indicative of an amorphous, non-crystalline material (see FIG. 7). The $^1$H-NMR spectrum was consistent with the expected structure, therefore no measurable degradation or dissociation of the product was observed. The glass transition of the amorphous material of Bimatoprost Acid Tromethamine Salt was determined as ca. 29° C. by modulated differential calorimetry (MDSC), no recrystallization was observed on further heating up to 100° C.

TABLE 2

Characterization of Amorphous Bimatoprost Acid Tromethamine Salt

| | |
|---|---|
| Compound | Bimatoprost Acid Tromethamine Salt |
| Process | Quenching the melt |
| XRPD | Amorphous |
| 1H-NMR | Consistent with structure. Stoichiometry 1.0:1.0 (Parent:Counterion) |
| MDSC | Tg at about 29° C. |

Polymorph Screening of Tromethamine Salt of Bimatoprost Acid:

A comprehensive polymorph screening study was performed on the tromethamine salt of bimatoprost. Polymorph screens were carried out using the supplied Form 1 and the prepared amorphous material as input materials. Analysis of all solids by XRPD showed that Form 1 was obtained from 29 out of 33 solvent systems. The salt did not recrystallize from water, acetic acid, ethanol/water (50/50 v/v) or acetone/water (50/50 v/v), under the conditions investigated. Vapor diffusion recrystallization experiments were also carried out and Form 1 was crystallized from 7 out of 35 experiments, all other experiments did not result in a crystalline form of tromethamine salt of bimatoprost acid.

I. Instrument and Methodology Details

A. X-Ray Powder Diffraction (XRPD)

X-Ray Powder Diffraction patterns were collected on a Bruker D8 diffractometer using Cu Ka radiation (40 kV, 40 mA), theta-2-theta goniometer, and divergence of V4 and receiving slits, a Ge monochromator and a Lynxeye detector. The instrument was performance checked using a certified Corundum standard (NIST 1976). The software used for data collection was Diffrac Plus XRD Commander v2.6.1 and the data were analyzed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° (2-theta);
Step size: 0.05° (2-theta); and,
Collection time: 0.5 sec./step.

Nuclear Magnetic Resonance (NMR):

NMR spectra were collected on a Bruker 400 MHz instrument equipped with an auto-sampler and controlled by a DRX400 console. Automated experiments were acquired using ICON NMR v4.0.4 running with Topspin v1.3 using the standard Bruker loaded experiments. For non-routine spectroscopy, data were acquired through the use of Topspin alone. Samples were prepared in DMSO-d6, unless otherwise stated. Off-line analysis was carried out using Topspin v1.3 or ACD SpecManager v12.5.

Differential Scanning Calorimetry (DSC):

DSC data were collected on a TA Instruments Q2000 equipped with a 50 position autosampler. The calibration for thermal capacity was carried out using sapphire and the calibration for energy and temperature was carried out using certified indium. Typically 3-3.5 mg of each sample, in an aluminum pan, was heated at 10° C./min from 25° C. to 130° C. A purge of dry nitrogen at 50 ml/min was maintained over the sample.

Modulated temperature DSC ("MDSC") was carried out using an underlying heating rate of 2° C./min and temperature modulation parameters of ±0.318° C. (amplitude) every 60 seconds (period). The instrument control software was Advantage for Q Series v2.8.0.394 and Thermal Advantage v5.2.6 and the data were analyzed using Universal Analysis v4.7A or v4.4A.

Thermo-Gravimetric Analysis (TGA):

TGA data were collected on a Mettler TGA/SDTA 851e equipped with a 34-position autosampler. The instrument was temperature calibrated using certified indium. Typically 5-30 mg of each sample was loaded onto a pre-weighed aluminum crucible and was heated at 10° C./min from ambient temperature to 350° C. A nitrogen purge at 50 mL/min was maintained over the sample. The instrument control and data analysis software was STARe v9.20.

Results of Polymorphism Study:

Bimatoprost acid tromethamine salt was fully characterized and was consistent with the reference material previously prepared for this compound, Form 1. Two screens were carried out with the maturation method using the supplied Form 1 and the amorphous material (previously prepared by the quenching the melt method) as starting material. At the end of the screens, only Form 1 polymorphic form was obtained from 25 out of 27 tested single-solvent systems and 4 out of 6 tested solvent mixtures.

Ophthalmic Preparations:

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water. The pharmaceutical compositions of the present invention may include a surfactant; however, surfactants are not necessary as surfactants are added to formulations to dissolve or increase solubility of the drug in formulation vehicles. In case of tromethamine salt, the solubility is high enough (~25 w/v %) so that no surfactant is needed.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

Ingredient Amount (% w/w) active ingredient about 0.001-5 preservative 0-0.10 vehicle 0-40 tonicity adjustor 0-10 buffer 0.01-10 pH adjustor q.s. pH 4.5-7.5 antioxidant as needed surfactant as needed purified water as needed to make 100%.

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for drop wise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 ml.

While this invention has been described with respect to these specific examples, it is understood that other modifications and variations are possible without departing from the spirit of the invention.

What is claimed is:

1. Tromethamine salt of bimatoprost acid in crystalline form having the XRPD pattern substantially as shown in FIG. 3.

2. Tromethamine salt of bimatoprost acid in crystalline form having XRPD peaks at the diffraction angles of about: 6.8°, 10.2°, 13.4°, 16.1°, 17.3°, 18.0°, 19.1°, 19.4°, 20.0°, 20.4°, 21.1°, 22.9°, 23.3°, 24.5°, 25.2° and 33.7° of 2-theta (Cu, K-alpha radiation).

3. Tromethamine salt of bimatoprost acid in crystalline form having a melting enthalpy from about 103.6 J/g to about 119.9 J/g.

4. Tromethamine salt of bimatoprost acid in crystalline form having a melting temperature within the range of about 104-110° C.

5. Tromethamine salt of bimatoprost acid in crystalline form having a melting temperature of about 105° C.

6. Tromethamine salt of bimatoprost acid in crystalline form having a melting temperature of about 105.6° C.

7. A pharmaceutical composition comprising a therapeutically effective amount of tromethamine salt of the bimatoprost acid in crystalline form of claim 2.

8. The pharmaceutical composition of claim 7 wherein the tromethamine salt of bimatoprost acid in crystalline form is in a pharmaceutically acceptable carrier.

9. The pharmaceutical composition of claim 8 wherein the pharmaceutically acceptable carrier is aqueous solution.

10. The pharmaceutical composition of claim 9 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.

11. The pharmaceutical composition of claim 8 wherein the pharmaceutically acceptable carrier is a solid dosage form.

12. The pharmaceutical composition of claim 11 wherein the solid dosage form is an ocular implant.

13. The pharmaceutical composition of claim 7 wherein the pharmaceutical composition may be used to treat one selected from the group consisting of elevated intraocular pressure, glaucoma, localized fat reduction or promotion of hair growth.

14. The pharmaceutical composition of claim 12 wherein the solid dosage form is used to treat elevated intraocular pressure or glaucoma.

15. The pharmaceutical composition of claim 9 wherein the bimatoprost acid in crystalline form is present in a concentration of 0.01% w/v to 0.1% w/v.

16. The pharmaceutical composition of claim 9 wherein the bimatoprost acid in crystalline form is present in a concentration of 0.03% w/v.

17. A method for treating ocular hypertension comprising administering to a subject in need thereof a therapeutically effective amount of the tromethamine salt of bimatoprost acid in crystalline form of claim 2, in an ophthalmically acceptable carrier.

18. The method of claim 17 wherein the ophthalmically acceptable carrier is selected from the group consisting of ophthalmically acceptable diluents, buffers, hydrochloric acid, sodium hydroxide, preservatives, stabilizers, tonicity adjustors, viscosity-enhancing agents, chelating agents, surfactants and/or solubilizers and combinations thereof.

19. The method of claim 17 wherein the tromethamine salt of bimatoprost acid in crystalline is dosed at least once a day.

20. The method claim 19 wherein the tromethamine salt of bimatoprost acid in crystalline form is dosed once a day.

* * * * *

UNITED STATES PATENT AND TRADEMARK OFFICE
CERTIFICATE OF CORRECTION

| | | |
|---|---|---|
| PATENT NO. | : 9,447,014 B2 | |
| APPLICATION NO. | : 14/137447 | |
| DATED | : September 20, 2016 | |
| INVENTOR(S) | : Thomas K. Karami et al. | |

It is certified that error appears in the above-identified patent and that said Letters Patent is hereby corrected as shown below:

On the Title Page

In item (57), in Column 2, in "Abstract", Line 4, after "compound" delete "is".

On the page 2, in Column 2, under "Other Publications", Line 1, delete "Prostagladin" and insert -- Prostaglandin --, therefor.

In the Specification

In Column 5, Line 8, delete "meaning" and insert -- meaning. --, therefor.

In Column 6, Line 27, delete "1H NMR" and insert -- $^1$H-NMR --, therefor.

In Column 6, Line 42, delete "(tromethamine),and" and insert -- (tromethamine), and --, therefor.

In Column 6, Line 45, delete "a a" and insert -- a --, therefor.

In the Claims

In Column 10, Line 50, in Claim 20, after "method" insert -- of --.

Signed and Sealed this
Twenty-eighth Day of November, 2017

Joseph Matal
*Performing the Functions and Duties of the
Under Secretary of Commerce for Intellectual Property and
Director of the United States Patent and Trademark Office*